United States Patent [19]

Lamberti

[11] 4,243,820

[45] Jan. 6, 1981

[54] METHOD FOR THE PREPARATION OF CARBOXYMETHYLOXYSUCCINIC ACID

[75] Inventor: Vincent Lamberti, Upper Saddle River, N.J.

[73] Assignee: Lever Brothers Company, New York, N.Y.

[21] Appl. No.: 905,628

[22] Filed: May 15, 1978

[51] Int. Cl.$^3$ ............................................. C07C 59/235
[52] U.S. Cl. ..................................... 562/583; 562/580
[58] Field of Search ................................ 562/580, 583

*Primary Examiner*—Paul J. Killos

*Attorney, Agent, or Firm*—James J. Farrell; Melvin H. Kurtz

[57] ABSTRACT

Carboxymethyloxysuccinic acid of improved purity may be prepared from its calcium salt by first precipitating the calcium as calcium carbonate by reaction with sodium carbonate, removing the calcium carbonate, acidifying the resulting solution of the sodium salt with sulfuric acid, extracting the free acid with a $C_4$ or $C_5$ alcohol or cyclohexanol and recovering the purified acid from the alcohol extracts.

4 Claims, No Drawings

METHOD FOR THE PREPARATION OF CARBOXYMETHYLOXYSUCCINIC ACID

This invention relates to an improvement in the production of carboxymethyloxysuccinic (CMOS) acid.

Carboxymethyloxysuccinic acid and its alkali metal salts are known to have utility as detergent builders, as described in U.S. Pat. No. 3,692,685. The acid is also a food acidulent, as described in U.S. Pat. No. 4,015,023.

The preparation of the calcium salt of CMOS is described in U.S. Pat. Nos. 3,692,685 and 3,914,297 both of which are hereby incorporated by reference. This reaction involves a Michael type addition of glycolic acid to maleic acid in the presence of calcium hydroxide.

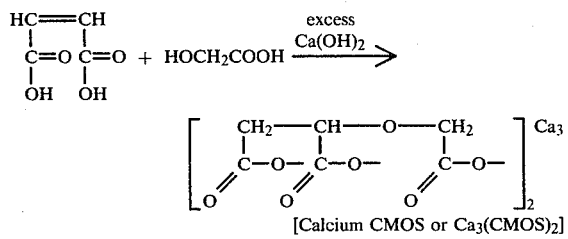

In order to obtain the free acid, the calcium salt is treated with a cation exchange resin.

Since the use of ion exchange resins is expensive for large scale production, improvements in this method have been made. U.S. Pat. No. 3,948,985 describes a method for the production of CMOS acid, i.e., $HOOCCH_2OCH(COOH)CH_2COOH$, involving the acidification of the calcium salt with sulfuric acid at a temperature of 40°–80° C., and removal of a precipitate of calcium sulfate dihydrate. It has been found, however, that the purity of the final product produced by this method as determined by NMR is not completely satisfactory.

It has now been discovered that CMOS acid of improved purity over that obtainable by prior art methods can be realized without the use of ion exchange resins by the following method of converting calcium CMOS to CMOS acid:

(a) reacting sodium carbonate and calcium CMOS in an aqueous medium;

(b) removing the resulting precipitate of calcium carbonate from the aqueous medium to form a solution of the sodium salt of CMOS, i.e., $Na_3CMOS$;

(c) acidifying the separated solution of $Na_3CMOS$ with sulfuric acid to form a solution of CMOS acid;

(d) extracting the CMOS acid from the acidified solution with a solvent which is a $C_4$ or $C_5$ alcohol or cyclohexanol: i.e., n-butanol, sec-butanol, isobutanol, tert-butanol, pentanol-1, pentanol-2, pentanol-3, 2-methyl-butanol-2, 2-methyl-butanol-3, 2-methyl-butanol-4, 2,2-dimethyl-propanol-1, cyclohexanol and mixtures thereof; and (e) separating the extracted CMOS acid from the extracting solvent.

Hereinafter, the solvents listed in (d) above will be referred to, individually and collectively, as the alcoholic solvent or solvents.

The above extraction of CMOS acid with n-butanol and 2-butanol was disclosed on May 17, 1977 at the 63rd Mid-Year Meeting of the Chemical Specalties Manufacturers Association held in Chicago, Illinois [see Soap Cosm. Chem. Spec. 53 (7) 34 (1977)]. Additionally, butanol is known in the extraction of other organic acids such as citric (French Pat. No. 1,211,066), malic and oxalic [Chem Abs. 38 5048 (1944)].

It has been found that the CMOS acid resulting from the instant procedure shows very high purity of NMR analysis, much higher than that of CMOS acid isolated from the reaction of sulfuric acid with calcium CMOS, followed by filtration according to the method of U.S. Pat. No. 3,948,985. Even if the CMOS acid prepared by the method of U.S. Pat. No. 3,948,985 is subjected to extraction by suitable organic solvents such as those employed by the instant invention, the CMOS acid isolated is still significantly less pure by NMR than the CMOS acid prepared according to the present invention. It is believed that the reaction of calcium CMOS with sodium carbonate, an essential step in the present invention, removes paramagnetic metal ion impurities, such as iron, thereby providing a high purity CMOS acid characterized by sharp well resolved NMR spectral bands. The process of U.S. Pat. No. 3,948,985, on the other hand, does not remove such impurities thereby leading to an impure CMOS acid characterized by broad NMR spectral bands.

A further disadvantage arises in attempting to prepare CMOS acid by extracting with organic solvents slurries of CMOS acid solutions and $CaSO_4$ which result from the acidification of $Ca_3(CMOS)_2$ with sulfuric acid. Such extractions tend to form persistent emulsions which are difficult to break and may require additional or undesirable treatments such as excessive dilution with water and heating, long separation times or centrifugation, and/or filtration of the $CaSO_4$ dihydrate prior to extraction or separation of the organic layer.

An additional advantage of the instant method is the usefulness of the by-products obtained. Calcium carbonate may easily be recycled in the reaction between maleic and glycolic acids to form calcium carboxymethyloxysuccinate. After the extraction of the CMOS acid with the alcoholic solvent, the water solution contains mainly sodium sulfate, which has utility as a detergent filler.

In the practice of the instant invention, the sodium carbonate may be added either as a powder, solution or aqueous slurry to the $Ca_3(CMOS)_2$ which may also be in the form of either a powder or aqueous slurry. Alternatively, the $Ca_3(CMOS)_2$, in either of the latter forms, may be added to an aqueous solution or slurry of sodium carbonate. The amount of sodium carbonate utilized is at least the stoichiometric amount based on calcium present and preferably about three to about three and one-half moles per mole of $Ca_3(CMOS)_2$. The temperature of the reaction medium during the precipitation of the calcium as calcium carbonate is not critical and may be about room temperature to about the boiling point of the reaction medium (i.e., 100° C. or higher depending on the level of dissolved solids present and whether pressures higher than atmospheric are utilized). Preferably it is desired to operate in the range from about 60° C. to about 100° C. in order to obtain reasonably fast filtering calcium carbonate particles.

After filtration of the calcium carbonate, the filtrate (and any washings of the $CaCO_3$) containing the trisodium salt of carboxymethyloxysuccinic acid, i.e., $Na_3C$-MOS, is generally cooled and then acidified with sulfuric acid. Alternatively, before acidification, the $Na_3C$-MOS may be isolated in solid form, either substantially anhydrous or as a hydrate, by conventional evaporation and drying or by crystallization from methanol/water or ethanol/water and especially according to the crystallization method described in Netherlands patent application No. 7,305,798. In utilizing solid Na$_3$CMOS in the instant invention, the Na$_3$CMOS or hydrate thereof is first dissolved in water. About 0.4 parts to about one part of water per part of the solid Na$_3$CMOS or hydrate thereof is utilized although this is not critical. The amount of water should be sufficient to form a solution and not excessive so as to require an inordinate number of extractions to remove the desired CMOS acid. The resulting aqueous solution of Na$_3$CMOS is then acidified with sulfuric acid, with cooling as required. The amount of sulfuric acid utilized is preferably about stoichiometric up to about 10% excess based on the Na$_3$CMOS and other alkaline salts that may be present. In terms of pH, the aqueous acidified solution may be at a pH of about 1 to about 4.

In the next step, a quantity of the alcoholic solvent, heretofore defined, is contacted with the acidified solution of Na$_3$CMOS in a batchwise or continuous manner with agitation. The mixture is then allowed to separate. If emulsions form, the mixture is warmed to facilitate separation of the phases. When the phases have separated, the alcoholic solvent layer containing the CMOS acid is removed. In the batchwise mode, the aqueous phase is then repeatedly extracted with more of the alcoholic solvent until the desired degree of removal of CMOS acid is attained. The extraction process may also be carried out continuously with the aforementioned alcoholic solvents by methods well known in the art.

The amount of alchoic solvent utilized relative to the acidified aqueous phase containing the CMOS acid is not critical and may vary from a weight ratio of about 0.1 to about 100 to 1 when the process is run batchwise. More practically it is desired to operate at a ratio of alcoholic solvent to aqueous layer from about 0.2 to 1 to about 3 to 1. When the process is carried out continuously the extraction may be run concurrently or preferably countercurrently by methods well known in the art.

The temperature of the extraction is not critical and may be carried out from about room temperature to about 10° C. below the boiling point of the alcoholic solvent utilized or a higher temperature may be utilized if the extraction is performed under pressure higher than atmospheric. Preferably it is desired to operate between about room temperature and about 60° C. to avoid any esterification side reactions which can occur between the alcoholic solvent and the CMOS acid on prolonged contact, particularly at the higher temperatures.

As an aid to the extraction step, inorganic salts preferably sodium sulfate, may be added to the acidified aqueous solution containing the CMOS acid. In this way, the CMOS acid is more easily extracted by virtue of the salting out effect produced by the inorganic salts. Use of Na$_2$SO$_4$ does not introduce any new compound and simply adds to the large amount of Na$_2$SO$_4$ already present in the acidified aqueous solution.

The alcoholic solvent may be removed from the CMOS acid dissolved therein by ordinary distillation or co-distillation with a liquid which is normally immiscible with the alcoholic solvent preferably water. These distillations may take place at atmospheric pressure, superatmospheric pressure or in vacuo. Co-distillation with water vapor, e.g. steam distillation is preferred to avoid spontaneous ester formation between the alcoholic solvents (especially the primary and secondary alcohols) and the CMOS acid. When vacuum distillation is employed, it is preferred to carry out the distillation in the presence of water or water vapor. Also, contact time is important since the esterification reaction can proceed even at room temperature in the cases of the primary and secondary alcohols. For this reason, prompt separation of the alcoholic solvent is desirable when using these alcohols. This separation is generally carried out within about 24 hours of the extraction step and preferably within about six hours for the best results. If the presence of esters of CMOS is tolerable, then depending on the tolerance the time restraints may be relaxed. Use of the tertiary alcohols of the invention (i.e. t-butanol and 2-methyl-butanol-2) will also minimize the need to employ the restraints described above particularly with respect to the esterification side reaction.

It is theorized that the esterification side reaction with CMOS in the presence of the alcoholic solvents of this invention arises because of the high acidity of the central carboxyl group of CMOS acid. It is theorized that citric acid, on the other hand, being a weaker acid than CMOS acid does not encounter this esterification problem to a significant degree with the same solvents.

The CMOS acid prepared by the instant process may be partially or completely neutralized in aqueous solution with suitable inorganic bases such as NH$_4$OH, NaOH, KOH, LiOH, Ca(OH)$_2$, Mg(OH)$_2$, Zn(OH)$_2$, etc. or organic bases such as monoethanolamine, diethanolamine, triethanolamine, isopropanolamine and the corresponding di- and tri-isopropanolamines. Such solutions contain the salts of CMOS in a high degree of purity with respect to carboxymethyloxysuccinate anion and are admirably suited for those purposes requiring such high purity (e.g. food, cosmetic and pharmaceutical). When making such salts of CMOS acid, the alcoholic solvent extract from the instant process may be directly treated with an aqueous solution or slurry containing a stoichiometric amount of the desired inorganic or organic bases to produce an aqueous layer containing the desired salt of CMOS acid. The aqueous layer may then be removed and evaporated or crystallized by conventional techniques to produce the anhydrous or hydrate forms of the corresponding salt of CMOS acid. When organic bases are utilized, it may be convenient to add the base directly to the alcoholic solvent extract and then evaporate the resulting reaction mixture to recover a residue of the organic amine salt of CMOS acid and a distillate of the alcoholic solvent. In the above cases when inorganic bases and organic bases are utilized and an aqueous layer is separated, the layer of alcoholic solvent may be recovered directly and returned to the CMOS acid extraction process without any need to employ distillation, an energy-consuming process.

The instant invention is further disclosed in the following examples and claims wherein all parts and proportions are by weight unless otherwise specified.

EXAMPLE 1

Preparation of Calcium CMOS

Maleic anhydride (19.6 g; 0.2 mole) is dissolved in 100 ml water at room temperature and stirred for 10–15 minutes to convert it to maleic acid. Glycolic acid (18.3 g; 0.24 mole) is added and dissolved with stirring. Calcium hydroxide (27 g; ca. 0.36 mole) sufficient to raise the pH to about 11.4 measured at 25° C., is added with vigorous stirring. The reaction mixture is heated to reflux and maintained at reflux for two hours. The resulting hot slurry of calcium CMOS product is then filtered to obtain a filter cake of $Ca_3(CMOS)_2$ which, after washing with water, is then dried or used directly for the extraction experiments described herein.

EXAMPLE 2

Preparation of CMOS Acid

Calcium CMOS, 24.1 g (containing 22.15% Ca) is slurried with 38 ml $H_2O$ and heated to 80° C. Sodium carbonate, 15.9 g (0.15 mole), is added and the temperature maintained at 80°–85° C. for 10 minutes. The mixture is filtered hot through Whatman #1 filter paper, and the filtered calcium carbonate washed twice with 5.6 ml of hot water. The resulting solution of $Na_3C$-MOS is acidified with concentrated sulfuric acid to a pH of 1.4, while cooling in an ice bath to 50° C. The acidified CMOS is extracted with five 25 ml portions of sec-butanol. Evaporation of the combined extracts in vacuo using co-distillation with water to remove the sec-butanol solvent provides a residue of CMOS acid amounting to 90.3% of theoretical based on the starting $Ca_3(CMOS)_2$.

EXAMPLE 3

Example 2 is repeated, except that 35 ml water are used in the slurry and two 15 ml portions of water are used to wash the calcium carbonate. 97.1% of the theoretical CMOS acid is obtained.

EXAMPLE 4

Calcium CMOS is converted to sodium CMOS by the addition of sodium carbonate as described in Example 2. The filtrate of $Na_3CMOS$ is evaporated in vacuo to give substantially anhydrous solid $Na_3CMOS$. 38.7 g of the solid $Na_3CMOS$ is slurried in 39.2 g water and 22.1 g concentrated sulfuric acid is added dropwise with stirring and cooling. The acidified mixture is extracted with five 50 ml portions of n-butanol. 93.9% of the theoretical CMOS acid is obtained.

EXAMPLE 5

Example 4 is repeated with extraction by secbutanol instead of n-butanol. 95.9% of the theoretical CMOS acid is obtained.

EXAMPLE 6

A mixture of $Na_3CMOS$, tetra- and pentahydrates, 30.55 g containing 76% active $Na_3CMOS$ and prepared by the reaction of $Ca_3(CMOS)_2$ with $Na_2CO_3$ and subsequent crystallization of the resulting $Na_3CMOS$ from methanol-water according to the method of Netherlands Patent Application No. 7,305,798, is dissolved in 23 g of water. The $Na_3CMOS$ solution is acidified with 13.8 g of 96% sulfuric acid while maintaining the temperature below 50° C. and then extracted with five consecutive 30 ml portions of t-butanol. Titration of the extracts with standard alkali show a recovery of 88.4% of the theoretical CMOS acid.

EXAMPLE 7

The procedure of Example 6 is repeated using 50.9 g of the $Na_3CMOS$ hydrates, 23.7 g of 96% $Na_2SO_4$, 25 g of water and five consecutive 50 ml portions of isobutanol in place of the quantities and the t-butanol cited in Example 6. The recovery of CMOS acid is 71.4% of the theoretical.

EXAMPLE 8

The procedure of Example 7 is repeated using five consecutive 25 ml portions of sec-butanol in place of the isobutanol. The recovery of CMOS acid is 76.0% of the theoretical.

EXAMPLE 9

The procedure of Example 7 is repeated except that five consecutive 50 ml portions of pentanol-1 are used in place of the isobutanol. Also, the temperature of the extraction is maintained at 47°–50° C. and small amounts of water are added during extraction to facilitate breaking of emulsions. The recovery of CMOS acid is 69.5% of the theoretical.

EXAMPLE 10

The procedure of Example 7 is repeated except that five consecutive 50 ml portions of pentanol-2 are used in place of the isobutanol and the temperature of the extraction is held at 40°–45° C. The recovery of CMOS acid is 82.0% of the theoretical.

EXAMPLE 11

The procedure of Example 10 is repeated except that five consecutive 50 ml portions of cyclohexanol are used in place of 2-pentanol. Breaking of emulsions is facilitated by raising the temperature to 50° C. and holding for a period of time as needed. The recovery of CMOS acid is 78.5% of the theoretical.

What is claimed is:

1. A method for the conversion of calcium carboxymethyloxysuccinate to carboxymethyloxysuccinic acid, comprising:
   (a) reacting calcium carboxymethyloxysuccinate with sodium carbonate in an aqueous medium;
   (b) removing the resulting precipitate of calcium carbonate from the aqueous medium to form a solution of the trisodium salt of carboxymethyloxysuccinic acid;
   (c) acidifying the separated solution of the trisodium salt of carboxymethyloxysuccinic acid with sulfuric acid to form a solution of carboxymethyloxysuccinic acid;
   (d) extracting the carboxymethyloxysuccinic acid from said aqueous solution with an alcoholic solvent selected from the group consisting of n-butanol, sec-butanol, isobutanol, tertbutanol, pentanol-1, pentanol-2, pentanol-3, 2-methyl-butanol-2, 2-methyl-butanol-3, 2-methyl-butanol-4, 2,2-dimethyl-propanol-1, cyclohexanol and mixtures thereof; and
   (e) separating the solvent from the extracted carboxymethyloxysuccinic acid.

2. A method as defined in claim 1 wherein said solvent is an alcohol of four carbon atoms or a mixture of four carbon atom alcohols.

3. A method as defined in claim 1 wherein said solvent is 2-methyl-butanol-2, tert-butanol or a mixture thereof.

4. A method as defined in claim 1 wherein the solvent is separated from the extracted carboxymethyloxysuccinic acid by co-distillation with water vapor.

* * * * *